(12) United States Patent
Koike et al.

(10) Patent No.: US 6,582,609 B2
(45) Date of Patent: Jun. 24, 2003

(54) SULFATE SALT OF QUINOLONECARBOXYLIC ACID DERIVATIVES AND THE USE THEREOF

(75) Inventors: Tomomi Koike, Tochigi (JP); Yasuhiro Aizawa, Nagano (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/182,445

(22) PCT Filed: Jan. 30, 2001

(86) PCT No.: PCT/JP01/00599

§ 371 (c)(1),
(2), (4) Date: Jul. 29, 2002

(87) PCT Pub. No.: WO01/57017

PCT Pub. Date: Aug. 9, 2001

(65) Prior Publication Data

US 2003/0013882 A1 Jan. 16, 2003

(30) Foreign Application Priority Data

Feb. 1, 2000 (JP) ......................................... 2000-023609

(51) Int. Cl.[7] .............................. C02F 1/52; C02F 1/58; C07D 401/10
(52) U.S. Cl. ........................................ 210/710; 544/363
(58) Field of Search ........................... 544/363; 210/710

(56) References Cited

U.S. PATENT DOCUMENTS 4,980,470 A  *  12/1990  Masuzawa et al.
4,997,943 A  *   3/1991  Iwata et al.
6,333,045 B1 *  12/2001  Yasueda et al.

FOREIGN PATENT DOCUMENTS

| CN | 1257073 | 6/2000 |
| EP | 230295 | 7/1987 |
| EP | 241206 | 10/1987 |
| JP | 11-209286 | 8/1999 |
| WO | 00/10570 | 3/2000 |

OTHER PUBLICATIONS

Shi et al, Chemical Abstract vol. 134, No. 86166, abstract for CN 1257073 (Jun. 21, 2000).*

* cited by examiner

Primary Examiner—Emily Bernhardt
(74) Attorney, Agent, or Firm—Oblon, Spivak, McClelland, Maier & Neustadt, P.C.

(57) ABSTRACT

A method of treating an industrial waste liquor containing 1-cyclopropyl-7-(3-methyl-1-piperazinyl)-6-fluoro-8-methoxy-1,4-dihydro-4-oxo-3-quinolinecarboxylic acid (gatifloxacin), comprising adding aqueous sulfuric acid to said liquor to form a sulfate of said gatifloxacin, and/or a hydrate of said sulfate; and the sulfate, and/or hydrate of said sulfate, made by said method.

7 Claims, No Drawings

SULFATE SALT OF QUINOLONECARBOXYLIC ACID DERIVATIVES AND THE USE THEREOF

TECHNICAL FIELD

The present invention relates to sulfate of 1-cyclopropyl-7-(3-methyl-1-piperazinyl)-6-fluoro-8-methoxy-1,4-dihydro-4-oxo-3-quinolinecarboxylic acid (International Nonproprietary Name: gatifloxacin), its use for recovering gatifloxacin and recovering method. Gatifloxacin is characterized by its chemical structure having an alkoxy group at 8-position, and is useful as an antimicrobial agent.

BACKGROUND TECHNOLOGIES

As a method of treating industrial waste liquor containing quinolonecarboxylic acid derivatives, it is common to recover by adsorbing effective ingredients onto synthetic adsorbent etc., or to dispose by directly incinerating waste liquor itself without performing such recovering procedure of the like.

The method of recovering effective ingredients from industrial waste liquor containing quinolonecarboxylic acid derivatives by using synthetic adsorbent etc. is complicated procedurally and not a good method, resulting also in a cause of steep rise in preparation cost. Also, the incinerating disposal of industrial waste liquor containing a large quantity of effective ingredients cannot be said to be a preferable method from the environmental preservation.

Hence, upon preparation of gatifloxacin, it is very useful in the industry to find out a method of advantageously recovering gatifloxacin industrially from waste liquor after preparation and regenerating it.

DISCLOSURE OF THE INVENTION

As a result of diligent investigation on a method of industrially recovering gatifloxacin useful as an antimicrobial agent under such situation, the inventors have found that, if forming sulfate of gatifloxacin in the waste liquor etc., allowing to sediment and separate, and then freeing from salt, gatifloxacin can be advantageously recovered industrially, leading to the completion of the invention.

The inventive gatifloxacin sulfate and its hydrate are novel compounds not described in the literature. The concrete preparing method lies in that aqueous sulfuric acid is added to acidity water or water-containing alcohol dissolved or suspended gatifloxacin, thereby sedimenting sulfate of gatifloxacin. If recrystallizing this further from, for example, water, hydrate of sulfate of gatifloxacin can be obtained.

Also, when recovering gatifloxacin from industrial waste liquor after preparation, aqueous sulfuric acid is added to acidity water-containing alcoholic solution dissolved gatifloxacin, thereby obtaining sulfate as sedimented crystals. These are collected by filtration and washed or recrystallized, and then dissolved or suspended into water. Following this, if the solution is made weak alkaline with aqueous solution of alkali such as sodium hydroxide, good-quality gatifloxacin is freed, thus enabling to recover. In addition, the recycling use is possible by adding sulfate to new preparing process without separating gatifloxacin, leaving as it is in alkaline solution.

BEST EMBODIMENT TO PUT THE INVENTION INTO PRACTICE

Moreover, the alcoholic organic solvent after recovery of gatifloxacin as sulfate can be recovered as a solvent containing no basic ingredients, hence efficient recycling use is possible.

EXAMPLE

In following, the invention will be illustrated in detail by describing examples and referential example, but it is not confined thereto.

Example 1

Manufacture of Preparative Sample of Sulfate

Into 200 mL of water were suspended 20 g of 1-cyclopropyl-7-(3-methyl-1-piperazinyl)-6-fluoro-8-methoxy-1,4-dihydro-4-oxo-3-quiolinecarboxylic acid, which was dissolved by adding 68% acetic acid (5 mL). To this solution, 35% sulfuric acid (10 mL) was added to make acidic. Then, the sedimented crystals were collected by filtration and washed with water.

The crystals obtained were recrystallized from 400 mL of water to obtain 18.4 g of ½ sulfate·⅔ hydrate of 1-cyclopropyl-7-(3-methyl-1-piperazinyl)-6-fluoro-8-methoxy-1,4-dihydro-4-oxo-3-quinolinecarboxylic acid.

Melting point: 212–215° C. (decomp).

Elemental analysis:

|  | C % | H % | N % |
|---|---|---|---|
| Calcd. For $C_{19}H_{22}FN_3O_4 \cdot \frac{1}{2}H_2SO_4 \cdot \frac{2}{3}H_2O$: | 52.87 | 5.46 | 9.74. |
| Found: | 53.00 | 5.57 | 9.99. |

MS (m/e):

375 $[C_{19}H_{22}FN_3O_4]^+$

344 $[C_{19}H_{22}FN_3O_4—OCH_3]^+$

331 $[C_{19}H_{22}FN_3O_4—CO_2]^+$

319 $[C_{19}H_{22}FN_3O_4—C_3H_6N]^+$

275 $[C_{19}H_{22}FN_3O_4—CO_2—C_3H_6N]^+$

260 $[C_{19}H_{22}FN_3O_4—CO_2—C_4H_9N]^+$

NMR ($^1$H-NMR: 400 MHz, DMSO-$d_6$): δ1.01–1.15 (7H, m, (—CH$_2$)$_2$ of cyclopropyl group, CH$_3$— of piperazine ring) 3.02–3.45 (7H, m, piperazine ring) 3.78 (3H, s, CH$_3$O—) 4.14–4.20 (1H, m, —CH= of cyclopropyl group) 7.75 (1H, d, J=11.7 Hz, 5-position CH of quinolone ring) 8.71 (1H, s, 2-position CH of quinolone ring)

Example 2

An ethanol filtrate containing 1-cyclopropyl-7-(3-methyl-1-piperazinyl)-6-fluoro-8-methoxy-1,4-dihydro-4-oxo-3-quinolinecarboxylic acid caused by recrystallization in Referential example 1 was warmed to 40° C., and 35% sulfuric acid was added dropwise to bring to pH 4, which was stirred for 2 hours at the same temperature.

The sedimented crystals were collected by filtration to obtain 22.8 g of sulfate of 1-cyclopropyl-7-(3-methyl-1-piperazinyl)-6-fluoro-8-methoxy-1,4-dihydro-4-oxo-3-quinolinecarboxylic acid.

Into 105 mL of water, 21 g of this sulfate were suspended and dissolved by adding 24.5% aqueous solution of sodium hydroxide.

This solution was recycled to hydrolyzing solution of next lot as it is.

Example 3

After 3.6 L of ethanol filtrate containing 29 g (content was calculated from recrystallization yield) of 1-cyclopropyl-7-

(3-methyl-1-piperazinyl)-6-fluoro-8-methoxy-1,4-dihydro-4-oxo-3-quinolinecarboxylic acid obtained by the procedure similar to Referential example 1 was warmed to 40° C., 35% sulfuric acid was added dropwise to bring to pH 4, which was stirred for 2 hours at 40 to 45° C.

The sedimented crystals were collected by filtration to obtain 27.9 g of sulfate of 1-cyclopropyl-7-(3-methyl-1-piperazinyl)-6-fluoro-8-methoxy-1,4-dihydro-4-oxo-3-quinolinecarboxylic acid.

Into 133 mL of water, 26.5 g of this sulfate were suspended and dissolved by adding 24.5% aqueous solution of sodium hydroxide. To the dissolved solution, 68% acetic acid was added to adjust to pH 8, which was stirred for 1 hour as it is and then stirred for 10 minutes of 80 to 84° C. The sedimented crystals were collected by filtration and then washed with water to obtain 6.5 g of 1-cyclopropyl-7-(3-methyl-1-piperazinyl)-6-fluoro-8-methoxy-1,4-dihydro-4-oxo-3-quinolinecarboxylic acid.

Example 4

After 1000 L of filtrate containing 3 kg (content was calculated from recrystallization yield) of 1-cyclopropyl-7-(3-methyl-1-piperazinyl)-6-fluoro-8-methoxy -1,4-dihydro-4-oxo-3-quinolinecarboxylic acid recrystallized using 2-propanol in place of ethanol was warmed to 40° C., 35% sulfuric acid was added dropwise to bring to pH 4, which was stirred for 2 hours at the same temperature.

The sedimented crystals were collected by filtration and then washed with 45 L of water in suspended state, thereby obtaining 3.03 kg of sulfate of 1-cyclopropyl-7-(3-methyl-1-piperazinyl)-6-fluoro-8-methoxy-1,4-dihydro-4-oxo-3-quinolinecarboxylic acid.

Referential Example 1

To 215 g of (1-cyclopropyl-6,7-fluoro-1,4-dihydro-8-methoxy-4-oxo-3-quinolinecarboxylate-$O^3$, $O^4$)bis(acetate-O)-borate were added 66.1 g of 2-methylpiperazine, 113 g of triethylamine and 403 g of acetonitrile, and the mixture was stirred overnight at room temperature.

The solvent was distilled off and, after added 1.24 L of 0.5% acetic acid, the mixture was stirred for 3 hours at 80 to 85° C. The reaction mixture was cooled and, after added 1 g of activated carbon, the mixture was stirred for 0.5 hours. The activated carbon was separated by filtration, and to the filtrate, 24.5% aqueous solution of sodium hydroxide was added to adjust to pH 8, which was then stirred overnight at 0 to 5° C.

The sedimented crystals were collected by filtration to obtain 191 g of crude crystals of 1-cyclopropyl-7-(3-methyl-1-piperazinyl)-6-fluoro-8-methoxy-1,4-dihydro-4-oxo-3-quinolinecarboxylic acid.

These crude crystals were recrystallized from 90% ethanol to obtain 160 g of 1-cyclopropyl-7-(3-methyl-1-piperazinyl)-6-fluoro-8-methoxy-1,4-dihydro-4-oxo-3-quinolinecarboxylic acid.

[Utilizability in the Industry]

The inventive sulfate of 1-cyclopropyl-7-(3-methyl-1-piperazinyl)-6-fluoro-8-methoxy-1,4-dihydro-4-oxo-3-quinolinecarboxylic acid (gatifloxacin) and its hydrate are novel acid adducts. It has become clear that, if forming sulfate of gatifloxacin from the waste liquor after preparation, separating and purifying by usual method, and then freeing, gatifloxacin can be advantageously recovered industrially.

The gatifloxacin recovered via sulfate can be brought to recycling use as a product. Moreover, the alcoholic organic solvent after recovery of sulfate can be recovered as a solvent containing no basic ingredients, hence efficient recycling application is possible.

What is claimed is:

1. A method of treating an industrial waste liquor containing gatifloxacin, comprising adding aqueous sulfuric acid to acidify said liquor, thereby forming a sulfate of said gatifloxacin, and/or a hydrate of said sulfate.

2. The method according to claim 1, wherein the industrial waste liquor is water or water-containing alcohol in which the gatifloxacin is dissolved or suspended.

3. The method according to claim 1, additionally comprising treating said sulfate or said hydrate of said sulfate with an alkali, whereby gatifloxacin is obtained.

4. The method according to claim 2, additionally comprising treating said sulfate or said hydrate of said sulfate with an alkali, whereby gatifloxacin is obtained.

5. A method of treating an industrial waste liquor containing gatifloxacin, comprising adding aqueous sulfuric acid to said liquor to form a sulfate of said gatifloxacin, and/or a hydrate of said sulfate, as a sediment; and recrystallizing the sulfate from water, whereby a hydrate of a sulfate of gatifloxacin is obtained.

6. A hydrate of the sulfate of gatifloxacin.

7. The ½ sulfate·⅖ hydrate of gatifloxacin.

* * * * *